United States Patent
Ejersbo Petersen

(10) Patent No.: US 11,604,154 B2
(45) Date of Patent: Mar. 14, 2023

(54) METHOD AND SYSTEM FOR PREDICTION OF CONCRETE MATURITY

(71) Applicant: SENSOHIVE TECHNOLOGIES ApS, Odense C (DK)

(72) Inventor: Tobias Ejersbo Petersen, Odense C (DK)

(73) Assignee: SENSOHIVE TECHNOLOGIES APS, Odense C (DK)

(*) Notice: Subject to any disclaimer, the term of this patent is extended or adjusted under 35 U.S.C. 154(b) by 266 days.

(21) Appl. No.: 16/792,029

(22) Filed: Feb. 14, 2020

(65) Prior Publication Data
US 2020/0182812 A1 Jun. 11, 2020

Related U.S. Application Data

(63) Continuation of application No. PCT/DK2018/050188, filed on Aug. 2, 2018.

(51) Int. Cl.
*G01N 25/20* (2006.01)
*G01N 33/38* (2006.01)

(52) U.S. Cl.
CPC .......... *G01N 25/20* (2013.01); *G01N 33/383* (2013.01)

(58) Field of Classification Search
USPC .......................................... 374/141, 53, 163
See application file for complete search history.

(56) References Cited

U.S. PATENT DOCUMENTS

| | | | |
|---|---|---|---|
| 5,041,987 A * | 8/1991 | Kuwahara | G01N 33/383 374/53 |
| 2007/0179653 A1 | 8/2007 | Trost et al. | |
| 2010/0324835 A1 | 12/2010 | Fox et al. | |
| 2014/0353864 A1 | 12/2014 | Grochoski | |
| 2022/0063133 A1 * | 3/2022 | Van Dixhorn | B28C 7/024 |

FOREIGN PATENT DOCUMENTS

| | | | |
|---|---|---|---|
| CN | 103605888 A | | 2/2014 |
| CN | 104807982 A | | 7/2015 |
| JP | 2011256061 A | | 12/2011 |
| KR | 20110091185 A | * | 8/2011 |
| KR | 101091870 B1 | * | 12/2011 |
| WO | WO2007025172 A2 | | 3/2007 |
| WO | WO2017031526 A1 | | 3/2017 |

OTHER PUBLICATIONS

International Patent Application No. PCT/DK2018/050188, International Search Report (ISR) and Written Opinion dated Dec. 11, 2018—11 pages.
Danish Patent Application No. PA 2017 00443, Search Report completed Nov. 6, 2017—4 pages.
Wang et al. (2011), "Prediction of temperature distribution in concrete incorporating fly ash or slag using a hydration model", Composites: Part B, vol. 42, Jan. 1, 2011, pp. 27-40.

* cited by examiner

*Primary Examiner* — Mirellys Jagan
(74) *Attorney, Agent, or Firm* — Lathrop GPM LLP

(57) ABSTRACT

A method for predicting the maturity of a concrete during the curing process is disclosed. The method comprises the following steps:
  predicting at least one future temperature within the concrete;
  performing at least one temperature measurement, preferably a real-time temperature measurement of the concrete;
  transmitting the at least one temperature measurement wirelessly from at least one temperature sensor to an external device; and
  determining the energy production within the concrete.

8 Claims, 7 Drawing Sheets

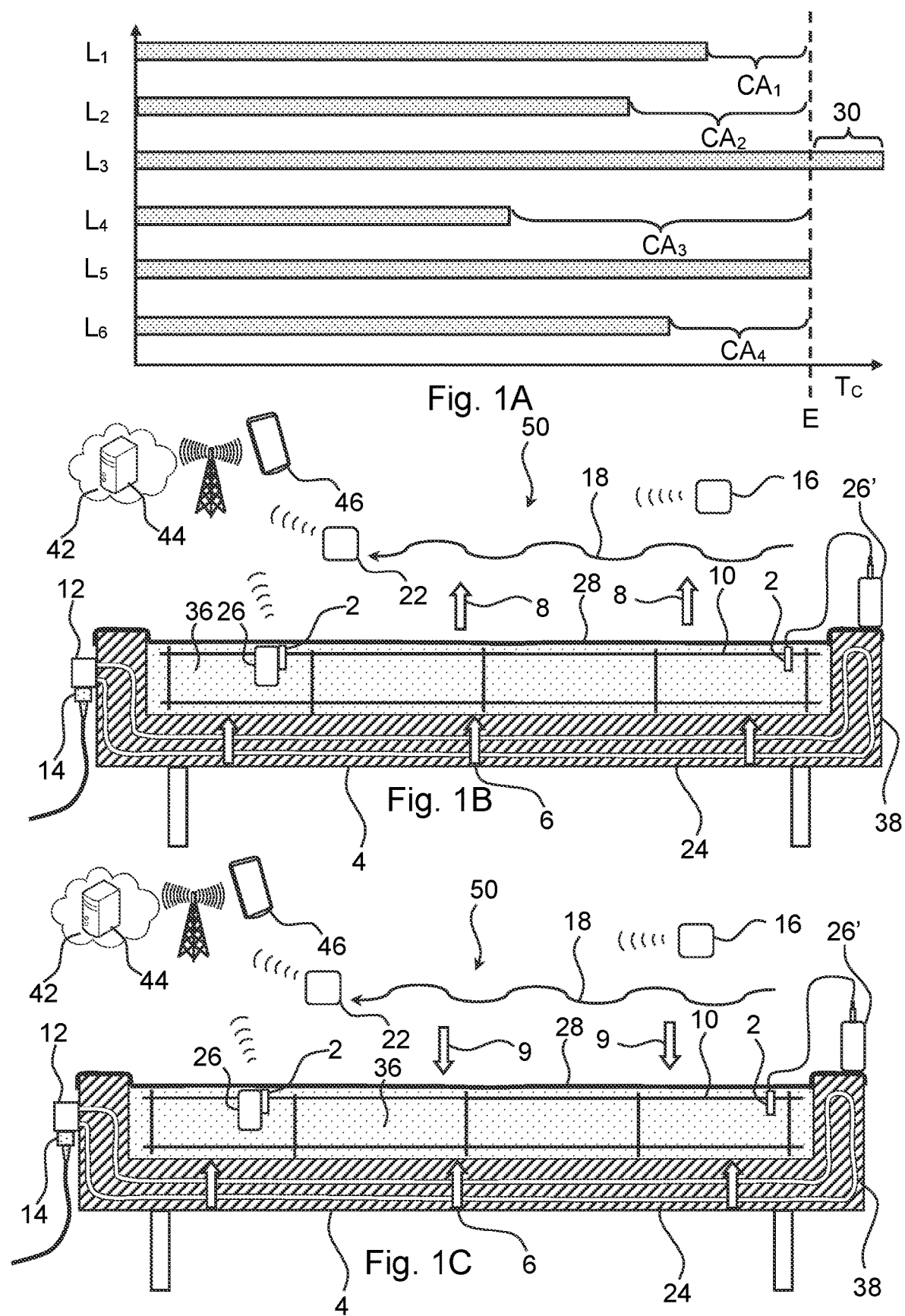

METHOD AND SYSTEM FOR PREDICTION OF CONCRETE MATURITY

CROSS-REFERENCE TO RELATED APPLICATIONS

This application is a continuation of International Patent Application No. PCT/DK2018/050188, filed Aug. 2, 2018, which claims the benefit of priority to Danish Patent Application No. PA 2017 00443 filed Aug. 15, 2017, each of which is incorporated herein by reference in its entirety.

FIELD OF INVENTION

The present invention relates to a method and a system for prediction of concrete maturity. The present invention more particularly relates to a method and a system for predicting early-stage strength and maturity in concrete.

PRIOR ART

Temperature and maturity monitoring of concrete is an important issue because concrete constructions are used in various construction areas. Curing is the hydration process that occurs after the concrete has been placed, allowing calcium-silicate hydrate to form. Concrete curing requires time in order to gain strength and harden fully. In the following the term "setting" is also used for "curing".

Optimum curing concrete leads to increased strength, whereas improper curing can cause scaling, reduced strength, poor abrasion resistance and cracking. Setting of cement is an exothermic process and the temperature is a key parameter that has significant impact on the process, since the process time is important for coordination of the entire production time in production situations e.g. in a production facility. Accordingly, it is important to carry out temperature and/or maturity measurements on a continuous basis in order to monitor the curing process.

Moreover, in concrete element production facility, optimum coordination of the different production lines is required to save time. Accordingly, it is desirable to be able to predict concrete maturity so that the preparation of the next project on a production line can be carried out in good time. Basically, time and money can be saved by being able to predict concrete maturity.

The strength of concrete according to its class of strength is defined as the strength achieved after 28 days curing in a curing frame at 20° C. The temperature, however, typically varies as function of time and is not kept at 20° C. at the entire time-period. The chemical reactions occurring during setting of cement depends on the temperature and the relationship between the reaction time and temperature, confer the below-mentioned formula:

$$\text{The relative velocity} = \frac{\text{The velocity at the actual temperature}}{\text{The velocity at 20° C.}} \quad (1)$$

The generated heat can be expressed as function of the maturity of the concrete. The maturity M is given by:

$$M = \sum_{i=1}^{n} H(\theta_i) \cdot \Delta t_i, \quad (2)$$

where $\Delta t_i$ is the length of the interval i;
$\theta_i$ is the mean temperature in the time interval i, and
$H(\theta_i)$ is the velocity function defined by the following equation:

$$H(\theta_i) = \exp\left[\frac{E(\theta)}{R} \cdot \left(\frac{1}{293} + \frac{1}{273+\theta}\right)\right], \quad (3)$$

where R is the gas constant 8.314 J/mol ° K;
$E(\theta)$ is the activation energy for the concrete mixture.

$$E(\theta) = 33.500 \text{ J/mol, for } \theta \geq 20° \text{ C.} \quad (4)$$

$$E(\theta) = 33.500 \text{ J/mol} + 1470 \cdot (20-\theta), \text{ for } \theta < 20° \text{ C.}, \quad (5)$$

Graphically, this can be expressed in the graph shown in FIG. 7A.

The duration of the setting depends on the concrete temperature. The relationship between the duration of the setting and the concrete temperature is shown in FIG. 7B.

The heat development Q is expressed as energy per kg cement and is determined by the following equations:

$$\Delta Q_n = \Delta Q_{acc,n} + \Delta Q_{trans,n} \quad (6)$$
$$= (\theta_{n+1} - \theta_n) \cdot C_c \cdot \frac{\rho_c}{C} +$$
$$\left[\frac{a_t \cdot \rho_c}{m_c \cdot C} \cdot \frac{f_{c,n} + f_{c,n+1}}{2} \cdot \Delta t_n\right]$$

$$Q = \sum_{n=1}^{N-1} \Delta Q_n, \quad (7)$$

where:
$\Delta Q_{acc,n}$ is the change of accumulated energy in the concrete during the interval $\Delta t_n$;
$\Delta Q_{trans,n}$ is the change of transmitted energy from the concrete to the surroundings during the time interval $\Delta t_n$;
$\theta_n$ and $\theta_{n+1}$ is the concrete temperature at the beginning and end of the time interval $\Delta t_n$;
C is the content of cement per m³ concrete measured in kg/m³;
$\rho_c$ is the density of concrete measured in kg/m³;
$C_c$ is the specific heat of the concrete;
$f_{c,n}$ and $f_{c,n+1}$ is the output from box wall transducer at the beginning and end of the time interval $\Delta t_n$;
$m_c$ is the weight of the concrete sample (measured in kg);
$a_t$ is a calibration factor, and
$\Delta t_n$ is the time interval=$t_{n+1} - t_n$ E.g. from US 2010/0324835 A1, a system for measuring mechanical data associated with the mechanical properties of a concrete mass using a mathematical approach, i.e. the Nurse-Saul maturity and the Arrhenius maturity, is known. The system includes a sensor and a logger electrically connected and embedded in the concrete mass. The system requires an electrically connected reader for obtaining data necessary for calculating the maturity of the concrete mass. Furthermore, data about the concrete type must be stored in the sensor prior to embedment in the concrete mass. Accordingly, the system is not sufficiently flexible and is further expensive as the sensor must have built-in electronics to store information and send detailed information.

Prediction of the early-stage (e.g. the first 18 hours) strength of concrete is essential for the manufacturing of structural parts. Economic and safe scheduling of such operations as form removal and reshoring and application of post-tensioning, and rapid delivery of products all are required to be based upon a good prediction of the strength development of the concrete in use. When manufacturing structural parts knowledge of the early-stage strength of concrete is of special importance. Accelerated curing is used to achieve high early age strength in concrete. Accelerated curing techniques are particularly useful in the prefabrication industry, wherein high early age strength enables a fast removal of the formwork (e.g. within 24 hours). Hereby it is possible to reduce the cycle time and save costs. Accelerated curing can be achieved by using active heating e.g. by means of a heating source such as warm water, steam or electric heating. A curing cycle typically involves a preheating stage (delay period) in the range between 2 to 5 hours, in which the temperature is increased until a predefined maximum temperature (e.g. within the range 50-82° C.) has been achieved. Hereafter the maximum temperature is maintained, where after a cooling period is provided. Preferably, the entire cycle should not exceed 18 hours. Early-stage strength and maturity prediction of concrete may be used to utilise the staff and production capacity in a more optimum manner in manufacturing of structural parts.

One of the challenges is that environmental (e.g. ventilation and heat exchange with surrounding structures) heavily influences the curing time. If a concrete production line comprises a supporting table that is heated, the concrete being poured into a frame supported by the supporting table will receive a high initial temperature. On the other hand, if the gates in a production hall are opened, the air temperature may suddenly drop, and an increased airflow may introduce a cooling of the concrete. All these factors are, at present, not taken into account. Accordingly, average curing times suitable under standard conditions are applied for lack of anything better. Unfortunately, this strategy sometimes leads to production of constructions with improper curing, which may cause scaling, reduced strength, poor abrasion resistance and cracking. These constructions are typically thrown away as waste. On the other hand, in many situations, the actual curing time is shorter than the estimated curing time. Accordingly, a lot of free capacity in production facilities are used because most production facilities use the principle: "better safe than sorry" meaning that safety-time is added to the estimated curing time in order to be "safe".

Thus, there is a need for a method and a system for prediction of concrete maturity.

It is an object of the invention to provide a method and a system for prediction of concrete maturity.

SUMMARY OF THE INVENTION

The object of the present invention can be achieved by a method as defined in claim 1 and a system as defined in claim 7. Preferred embodiments are defined in the dependent subclaims, explained in the following description and illustrated in the accompanying drawings.

The method according to the invention is a method for predicting the maturity of concrete during the curing process, wherein the method comprises the following steps:
  predicting at least one future temperature within the concrete;
  performing at least one temperature measurement, preferably a real-time temperature measurement of the concrete;
  transmitting the at least one temperature measurement wirelessly from at least one temperature sensor to an external device such as a server via the Internet;
  determining the energy production within the concrete;

Hereby, it is possible to provide a method for prediction of concrete maturity. The method can be used to predict strength, production time and maturity target reached temperature. Accordingly, by applying the method according to the invention it is possible to save time (using free capacity at productions lines) and to avoid errors made by applying too short curing periods. It is also possible to alert the risk for exceeding a predefined maximum allowable temperature limit before the temperature is exceeded. The method according to the invention makes it possible to detect that a too high temperature will be achieved if the heating process is continued. Accordingly, it is possible to turn off an external heating source and/or activate a cooling unit in order to regulate the temperature and avoid that that the temperature exceeds the maximum allowable temperature limit.

The method can be used to predict the future maturity of the concrete during the curing process and the remaining production time. By displaying this piece of information e.g. in a large production facility, it is possible to enable and initiate new productions (e.g. starting up production on a production line, in which the strength of the construction is so enough that the construction may be removed) much faster than today. Moreover, errors can be eliminated because measurements are carried out to make sure that the curing process has reached a predefined acceptable level.

The step of predicting at least one future temperature within the concrete is preferably carried out by using information about the relationship between temperature and heat generation in concrete.

The step of performing at least one temperature measurement, preferably a real-time temperature measurement of the concrete, is carried out by using one or more temperature sensors.

In a preferred embodiment according to the invention the method is applied for prediction of maturity of the concrete during the early-stage curing process.

In one embodiment according to the invention, the at least one temperature measurement, is carried out by using one or more temperature sensors comprising one or more thermocouples embedded into the concrete.

The step of determining the energy production within the concrete is preferably carried out by applying information about the temperature of the concrete.

It may be an advantage that the method comprises the step of determining one or more environmental parameters. The one or more environmental parameters may be measured by using one or more sensors.

The one or more environmental parameters may be one or more of the following:
  the temperature of a supporting structure (e.g. a table supporting a concrete construction;
  the environmental humidity;
  ventilation measurement(s) such as airflow (velocity) and/or temperature that may influence the temperature of the concrete.

It may be advantageous that the determination of the energy production within the concrete is performed by using the flowing formula:

$$\Delta Q_n = \Delta Q_{acc,n} + \Delta Q_{trans,n}$$
$$= (\theta_{n+1} - \theta_n) \cdot C_c \cdot \frac{\rho_c}{C} +$$

-continued
$$\left[\frac{a_t \cdot \rho_c}{m_c \cdot C} \cdot \frac{f_{c,n} + f_{c,n+1}}{2} \cdot \Delta t_n\right]$$

where:

$\Delta Q_{acc,n}$ is the change of accumulated energy in the concrete during the interval $\Delta t_n$;

$\Delta Q_{trans,n}$ is the change of transmitted energy from the concrete to the surroundings during the time interval $\Delta t_n$;

$\theta_n$ and $\theta_{n+1}$ is the concrete temperature at the beginning and end of the time interval $\Delta t_n$;

C is the content of cement per m³ concrete measured in kg/m³;

$\rho_c$ is the density of concrete measured in kg/m³;

$C_c$ is the specific heat of the concrete;

$f_{c,n}$ and $f_{c,n+1}$ is the output from box wall transducer at beginning and end of the time interval $\Delta t_n$;

$m_c$ is the weight of the concrete sample (measured in kg);

$a_t$ is a calibration factor, and $\Delta t_n$ is the time interval=$t_{n+1}$-$t_n$ The heat development Q within the concrete can be calculated by using the following formula:

$$Q = \sum_{n=1}^{N-1} \Delta Q_n,$$

It may be beneficial that the environmental parameters are saved to form historical data.

The environmental parameters may be stored in any suitable storage unit, e.g. on a server being accessible via the Internet.

It may be an advantage that the environmental parameters include:
  one or more environmental temperatures and/or
  one of more air circulation measurements and/or
  one or more humidity measurements.

As used within the present context, the expression "and/or" is intended to mean "and", "or" as well as both. By way of example, the expression is intended to include e.g. one or more environmental temperature, and one or more air circulation measurements, and one or more humidity measurements, one or more environmental temperature, or one or more air circulation measurements, or one or more humidity measurements, as well as other combinations with "and" or "or".

As used within the present context, the expression "one or more" is intended to mean at least one, and more than one such as two, three, four, five or six, by way of example.

These parameters are easy to measure by using one or more sensors. Moreover, these parameters influence the concrete and thereby the heat generation of the concrete.

It may be advantageous that at least some of the historical data are used for predicting at least one future temperature within the concrete.

Hereby, it is possible to perform a better and more accurate prediction.

The system according to the invention is a system for predicting the maturity of the concrete during the curing process, wherein the system comprises:
  a predicting unit configured to predict at least one future temperature within the concrete;
  at least one temperature sensor configured to perform temperature measurements, preferably real-time temperature measurements of the concrete;
  an energy production estimator configured to estimate the energy production within the concrete,
  wherein the at least one temperature sensor is arranged and configured to transmit the collected data wirelessly to an external device such as a server via the internet.

Hereby, it is possible to provide a system for prediction of concrete maturity. The method can be used to predict strength, production time and maturity target reached temperature. Accordingly, by applying the system according to the invention it is possible to save time (using free capacity at productions lines) and to avoid errors made by applying too short curing periods.

The predicting unit may be formed as a processing unit e.g. being part of a computer or another electrical device configured to carry out the required calculations. In one embodiment according to the invention, the system comprises a web-based predicting unit that may be provided in a server accessible via the Internet.

The predicting unit is configured to predict at least one future temperature within the concrete.

The system comprises at least one temperature sensor configured to perform temperature measurements, preferably real-time temperature measurements of the concrete. The temperature sensor may be any suitable type of temperature sensor capable of detecting the temperature of the concrete.

In one embodiment according to the invention, the at least one temperature measurement, is carried out by using one or more temperature sensors comprising one or more thermocouples embedded into the concrete.

The system comprises an energy production estimator configured to estimate the energy production within the concrete. The energy production estimator may be formed as a processing unit e.g. being part of a computer or another electrical device configured to carry out the required calculations. In one embodiment according to the invention, the system comprises a web-based energy production estimator that may be provided in a server accessible via the Internet.

It may be advantageous that the system comprises:
  one or more environmental parameter determination units configured to determination one or more environmental parameters influencing the temperature of the concrete;

Hereby, it is possible to take one or more environmental parameters influencing the temperature of the concrete into account in future predictions. Accordingly, the method according to the invention may gradually be improved as time goes by.

The one or more environmental parameter determination units may be configured to determine (e.g. measure) one or more of the following:
  the temperature of a supporting structure such as a table;
  environmental humidity;
  and/or ventilation measurement(s) such as airflow (velocity) and temperature) influencing the temperature of the concrete.

It may be beneficial that the system is configured to store one or more environment parameters to form historical data.

Hereby, the environmental parameters forming historical data can be used to improve the accuracy of the system It may be an advantage that the system is configured to predict at least one future temperature within the concrete on the basis of the historical data.

It may be preferred that real-time temperature measurements of the concrete are carried out on a continuous basis.

It may be advantageous that real-time temperature measurements of the concrete are carried out on a continuous basis by using temperature sensors and a thermocouple electrically connected to said sensors.

It may be an advantage that the temperature measurements are carried out by using a voltage sensor configured to measure the electric potential difference between two dissimilar conductors of the thermocouple cable.

DESCRIPTION OF THE DRAWINGS

The invention will become more fully understood from the detailed description given herein below. The accompanying drawings are given by way of illustration only, and thus, they are not limitative of the present invention. In the accompanying drawings:

FIG. 1A shows a schematic view of the setting time of concrete constructions produced on six production lines;

FIG. 1B shows a cross-sectional view of a concrete construction being made by means of a casting frame in a production facility, in which the concrete emits heat to air above the concrete;

FIG. 1C shows a cross-sectional view of the concrete construction shown in FIG. 1B, in a situation, in which the concrete receives heat from the air above the concrete;

DETAILED DESCRIPTION OF THE INVENTION

Figure 2B:
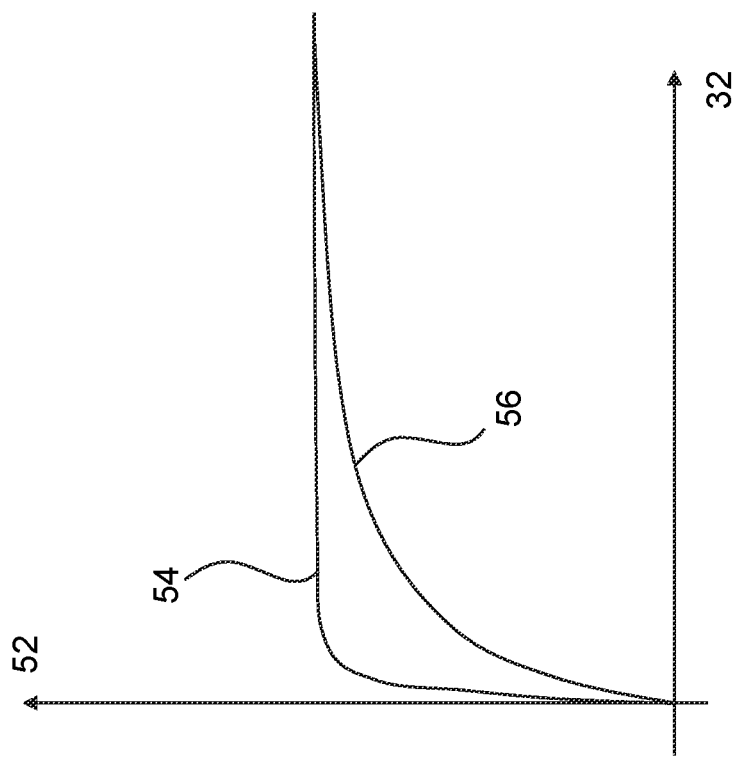
FIG. 2B shows a curve for a standard curing process and an accelerated curing process.

Referring now in detail to the drawings for the purpose of illustrating preferred embodiments of the present invention, FIG. 1A illustrates a schematic view of the curing time $T_c$ (setting time) of concrete constructions produced on six production lines $L_1$, $L_2$, $L_3$, $L_4$, $L_5$, $L_6$ arranged in a production facility to produce the same construction.

The curing time TC of the production lines $L_1$, $L_2$, $L_3$, $L_4$, $L_5$, $L_6$ is indicated by boxes filled with dots. The estimated (safe) curing time E is indicated on the curing time axis. It can be seen, that the curing time of the first production line $L_1$ is shorter than the estimated (safe) curing time E. Accordingly, there is a "capacity available" $CA_1$. This means that the construction process of the first production line $L_1$ could have been terminated and a new production process could have been initiated. Accordingly, time could have been saved.

The curing time of the second production line $L_2$ is even shorter than the curing time of the first production line $L_1$ and therefore also shorter than the estimated curing time E. Therefore, there is a "capacity available" $CA_2$ and the construction process of the production line $L_2$ may have been terminated in order to initiate a new production process.

The curing time of the third production line $L_3$ is longer than the estimated curing time E. Therefore, a construction process is actually terminated before the construction has received the required maturity and strength. Accordingly, the construction cannot be used and will therefore be waste.

The curing time of the fourth production line $L_4$ is shorter than the curing time of the first production lines $L_1$ and $L_2$ as well as the estimated curing time E. Thus, there is a "capacity available" $CA_3$ and the construction process of the production line $L_4$ could have been terminated in order to use the production line $L_4$ and initiate a new production process.

The curing time of the fifth production line $L_5$ corresponds to the estimated curing time E.

The curing time of the sixth production line $L_6$ is shorter than the estimated curing time E. Accordingly, there is a "capacity available" $CA_4$ and the construction process of the production line $L_6$ may have been terminated in order to initiate a new production process.

FIG. 1A illustrates that even when constructing the same construction, environmental influences makes it very difficult to estimate the curing time. Even though an additional safety-time is added to the estimated curing time E errors occur. Furthermore, a lot of time is wasted.

FIG. 1B illustrates a cross-sectional view of a concrete construction being made by means of a casting frame 38 in a production facility, in which the concrete 36 emits heat 8 to the surrounding air above the foil 28 covering the top side of the concrete 36. The casting frame 38 is part of a support unit 4 shaped as a table with legs and an integrated heating unit 24 comprising electrical heating wires supplied with power from an electrical connection (socket) 12 connected to a power supply by means of an electric plug 14. Alternatively, heating tubes may be arranged and configured to circulate a heating fluid (e.g. water) inside the casting frame 38.

The heating unit 24 generates heat 6 that is transferred to the concrete 36 in order to initiate or speed op the curing process. A system 50 according to the invention is applied to monitor the concrete construction process on a continuous basis. The system 50 comprises two sensors 26, 26' arranged to monitor the temperature inside the concrete 36. Each sensor 26, 26' measures the temperature of the concrete 36. The first sensor 26' measures the temperature of the concrete 36 by means of a cable 20 comprising a thermocouple embedded in the concrete 36. The other sensor 26 is embedded in the concrete and measures the temperature of the concrete 36 and sends a wireless signal to a receiving unit. The cable 20 and the sensor 26 are attached to an elongated body (a rebar) 10 embedded in the concrete 36.

The system 50 comprises a humidity sensor 16 arranged to measure the humidity of the surrounding air. The system 50 also comprises an airflow (velocity) sensor 22 arranged and configured to measure the flow of the circulating air 18 surrounding the top portion of the concrete 36.

The sensors 16, 22, 26, 26' are arranged and configured to transmit the collected data wirelessly to an external device such as a server 44 via the Internet 42. The sensors 16, 22, 26, 26' may be configured to communicate directly with an external device such as a smartphone 46. The smartphone 46 may communicate wirelessly with the Internet 42 and/or an Internet-based server 44.

FIG. 1C illustrates a cross-sectional view of the concrete construction shown in FIG. 1B, in a situation, which the concrete 36 receives heat 9 from the air above the concrete 36.

Figure 2A:
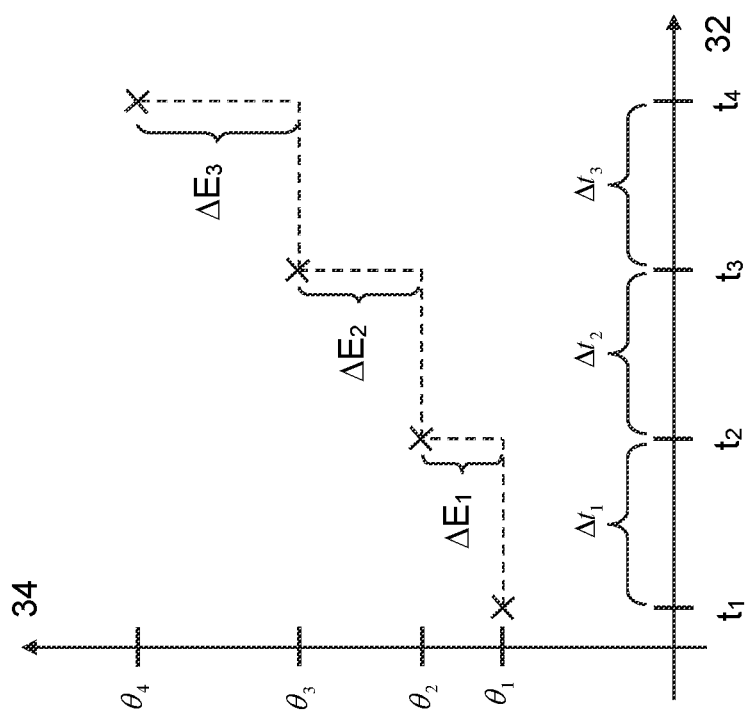
FIG. 2A shows a graph depicting measurement values from a calorimetric test, in which temperature is shown as function of time.

FIG. 2A illustrates a graph depicting measurement values from a calorimetric test (e.g. a Quasi-adiabatic test), in which temperature 34 is shown as function of time 32.

A Quasi-adiabatic test makes it possible to estimate the heat being released due to the hydration of cement contained in the concrete specimen. The test incorporates all possible interactions between concrete components, including the effects of admixtures.

The calorimeter used for carrying out the test is typically a double-walled caisson filled with an insulating material (e.g. polyurethane foam). The external wall may be made of polyvinyl chloride (PVC) and the internal wall may be of fiberglass-reinforced polyester.

The test is conducted on the concrete compound in order to be able to perform temperature predictions using the test results. The test determines the produced energy from the exotherm process in the concrete as a function of the maturity in the concrete. The test may be conducted in accordance with standards such as the "NT BUILD 388" standard or the "DS 423.37" e.g. a Quasi-adiabatic calorimetry test.

The method according to the invention applies the information about, how energy development in the concrete occurs as function of time and the method applies real-time measurements in the concrete as well as the environment. This information makes it possible to isolate the environmental factor from the structures surrounding the concrete and assess the influence this will have on the future development (curing process).

The duration $\Delta t_1$ of the first time interval ($t_1$ to $t_2$) equals the duration $\Delta t_2$ of the second time interval ($t_2$ to $t_3$) and the duration $\Delta t_3$ of the third time interval ($t_3$ to $t_4$). The time intervals $\Delta t_1$, $\Delta t_2$, $\Delta t_3$ may e.g. be 60-1200 seconds, such as 120-900 seconds, preferably 300-900 seconds such as 450-800 second. In one test scenario, the time intervals $\Delta t_1$, $\Delta t_2$, $\Delta t_3$ are 600 seconds.

Example 1

In one example, the following values may be recorded:
$\Delta t_1$, $\Delta t_2$, $\Delta t_3$=600 seconds;
$\Delta E_1$=320 Joule, $\Delta E_2$=540 Joule, $\Delta E_3$=920 Joule;
$\theta_1$=25° C., $\theta_2$=27° C., $\theta_3$=30° C., $\theta_4$=38° C.;

The quasi-adiabatic test identifies the amount of generated energy within the concrete in a 100% isolated environment. This reveals the relationship between the energy development and maturity of the concrete in a 100% isolated environment.

FIG. 2B illustrates a curve 56 for a standard curing process as well as a curve 54 for an accelerated curing process, in which the strength 52 is plotted as function of time 32. The curing process is typically considered to be accomplished after 28 days. The initial inclination of the curve 56 for the standard curing process is lower than the initial inclination of the curve 54 for the accelerated curing process. Accordingly, application of the accelerated curing process enables a much faster removal of construction produced e.g. in a production concrete panel factory.

Figure 3B:
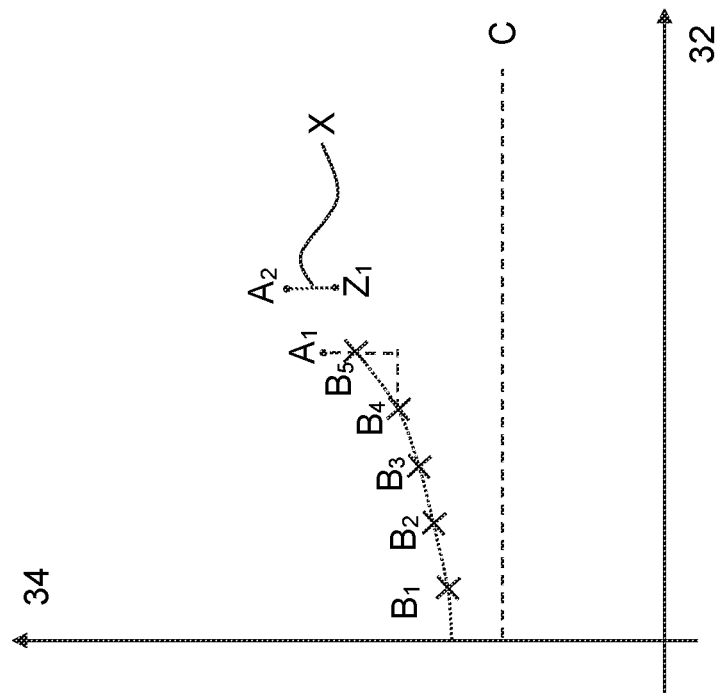
FIG. 3B shows another example of, how the method according to the invention can be used to adjust the environmental influence to predict the temperature development and hereafter the maturity and corresponding strength of the concrete.
Figure 3A:
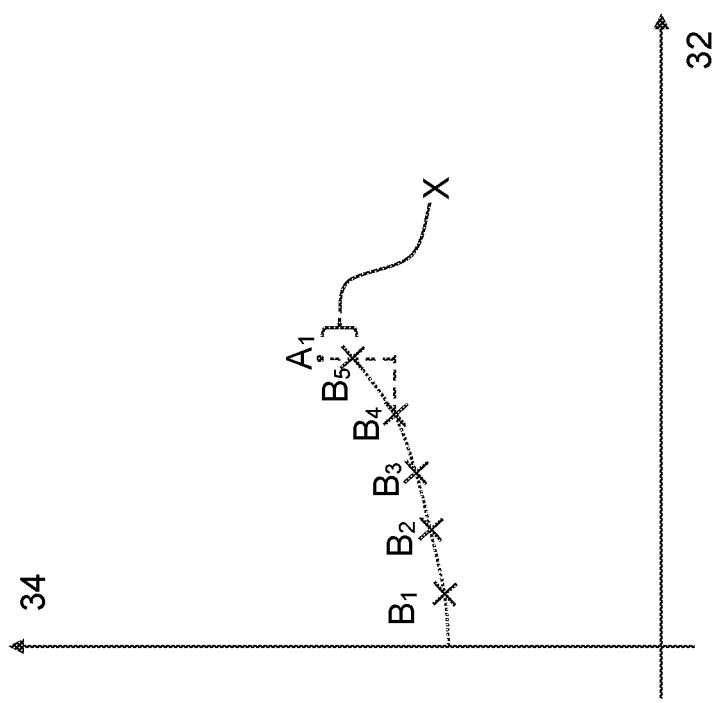
FIG. 3A shows an example of, how the method according to the invention can be used to adjust the environmental influence to predict the temperature development and hereafter the maturity and corresponding strength of the concrete.

FIG. 3A illustrates a graph depicting measurement values during a concrete curing process, in which temperature 34 is shown as function of time 32. Four first measurement points $B_1$, $B_2$, $B_3$, $B_4$ are plotted in the graph. The theoretical point (calculated assuming 100% insulation) $A_1$ is plotted next to these points. A fifth measurement point $B_5$ is plotted in the graph below the theoretical point $A_1$. The difference between the fifth measurement point $B_5$ and the theoretical point $A_1$ is caused by environmental influence X. When using the method according to the invention, temperature measurements of the concrete are carried out (preferably in real-time). Accordingly, it is possible to calculate the maturity of the concrete and match that with the energy development in the concrete. This enables determination of the amount of energy developed in the concrete, which energy can be correlated with the actual temperature development.

FIG. 3B illustrates an example of, how the method according to the invention can be used to adjust the environmental influence to predict the temperature development and hereafter the maturity and corresponding strength of the concrete. The graph comprises the same points as the graph shown in FIG. 3A, however a projected point $Z_1$ is added. The projected point $Z_1$ is estimated by using the method according to the invention applying the steps shown in the flowchart shown in FIG. 4. It can be seen, that the projected point $Z_1$ is below the theoretical point $A_2$ (assuming 100% insulation). The difference between the projected point $Z_1$ and the theoretical point $A_2$ is caused by environmental influence X. The environmental temperature C is shown in FIG. 3B.

In one embodiment according to the invention, the method comprises the step of collecting environmental influence data. Hereby, it is possible to apply the data to improve the prediction precession of the method.

In one embodiment according to the invention, the temperature of a support unit (e.g. a table) can be measured and collected (and preferably stored in a data storage). This temperature influences the curing process and may therefore be used to perform optimized future predictions.

In one embodiment according to the invention, the humidity of the surrounding air is measured and stored in a data storage. The specific heat capacity of humid air is greater than dry air and humid air will take more energy to heat by a given amount. Accordingly, the humidity of the surrounding air influences the curing process and may therefore be used to perform optimized future predictions.

In one embodiment according to the invention, the velocity of an airflow adjacent to the concrete and/or the frame, into which the concrete is poured, is measured and stored in a data storage. The velocity of an airflow adjacent to the concrete and/or the frame influences the curing process. Accordingly, the velocity of an airflow adjacent to the concrete and/or the frame may therefore be used to perform optimized future predictions.

In a preferred embodiment according to the invention, the temperature C of the surroundings is measured and stored in a data storage on a continuous basis. The temperature of the surroundings influences the curing process and therefore, it may be advantageous to apply the temperature of the surroundings to perform optimized future predictions.

Figure 4:
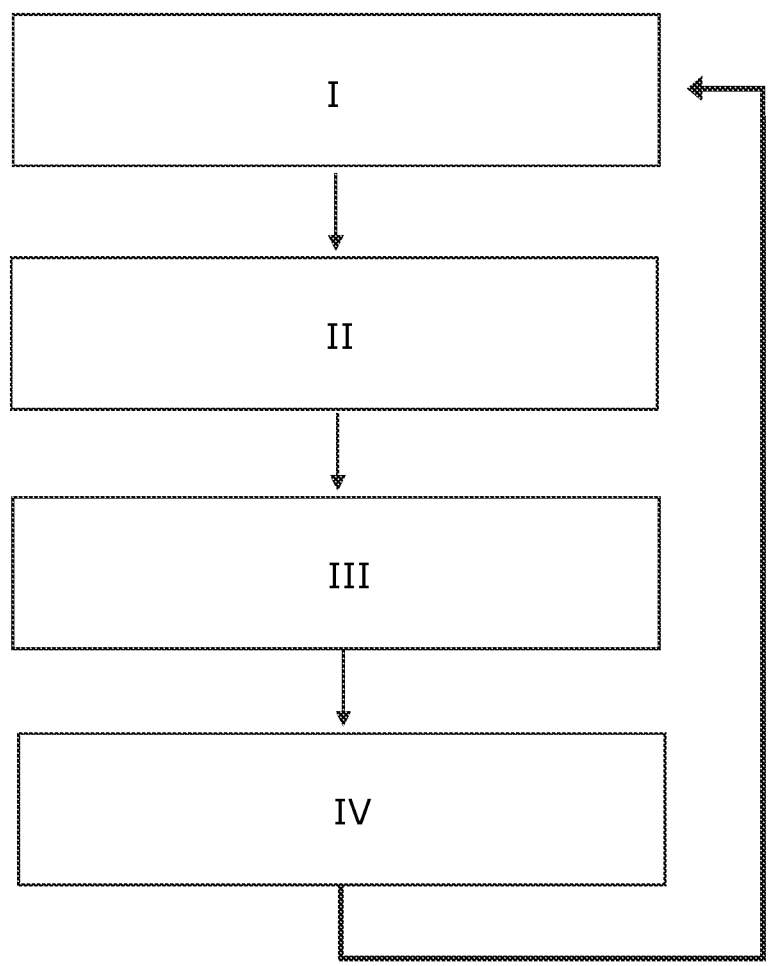
FIG. 4 shows a flowchart illustrating the steps carried out to predict the maturity of concrete according to one embodiment of the method of the invention.

FIG. 4 illustrates a flowchart illustrating the steps carried out to predict the maturity of concrete according to one embodiment of the method of the invention. Step I is a step of calculating the maturity of the concrete. Step I is carried out on the basis of an estimated temperature (carried out in Step four IV). Initially, when no temperature is estimated (in Step four IV), measured temperature values are applied. The temperatures are preferably measured by means of temperature sensors embedded in the concrete.

Step II represents the step of projecting the internal energy generated inside the concrete. This can be applied by using the previously mentioned equation (6):

$$\Delta Q_n = \Delta Q_{acc,n} + \Delta Q_{trans,n} \quad (6)$$

$$= (\theta_{n+1} - \theta_n) \cdot C_c \cdot \frac{\rho_c}{C} +$$

$$\left[ \frac{a_t \cdot \rho_c}{m_c \cdot C} \cdot \frac{f_{c,n} + f_{c,n+1}}{2} \cdot \Delta t_n \right]$$

Step III represents the step of applying environmental influencing factors. This step may include applying information about the temperature of a support unit (e.g. a table), the humidity of the surrounding, the velocity of an airflow adjacent to the concrete and/or the frame, the temperature of the surroundings.

Step IV represents the step of estimating concrete temperature. This is effected by using historic data collected, preferably in the production facility and even better in the actual production line within the production facility.

Performing an analysis on the historical data enables the method according to the invention to take into account the influences (e.g. the temperature of a support unit (e.g. a table) and/or the humidity of the surrounding and/or the velocity of an airflow adjacent to the concrete and/or the frame and/or the temperature of the surroundings) of the environment in which the concrete is manufactured. Accordingly, the historical data can be used to improve the prediction of the future temperature development.

The process for estimating the next data point is illustrated by the flowchart: The current maturity is calculated in Step I, the energy development is determined in Step II, the environment is accounted in Step III. Step III makes it possible to derive at the next temperature point in Step IV.

The process steps illustrated in FIG. 4 can now be repeated. Hereby, it is possible to estimate the remaining temperature development as illustrated in FIG. 5.

Each repetition may factor in the new maturity and the corresponding energy development in the concrete. The environmental influence is adjusted according to surrounding parameters such as temperature, humidity and air circulation.

Figure 5:
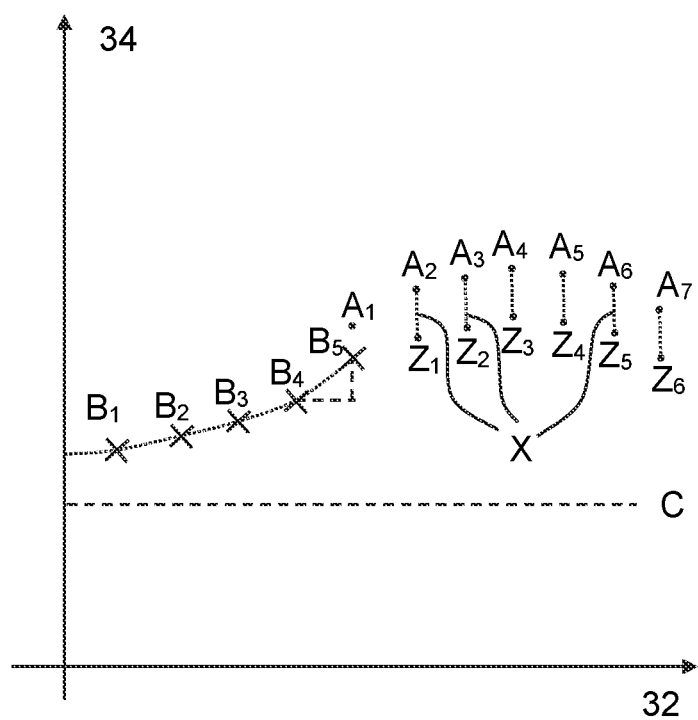
FIG. 5 shows an example of, how the method according to the invention can be used to adjust the environmental influence to predict the temperature development and hereafter the maturity and corresponding strength of the concrete.

FIG. 5 illustrates an example of, how the method according to the invention can be used to adjust the environmental influence to predict the temperature development and hereafter the maturity and corresponding strength of the concrete.

The graph depicts concrete temperature as function of time. The first portion of the graph corresponds to the graph shown in FIG. 3B. Further points have been added. These points are: $A_3$, $A_4$, $A_5$, $A_6$, $A_7$, $Z_2$, $Z_3$, $Z_4$, $Z_5$ and $Z_6$ corresponding to the "remaining" curing period.

Once the temperature development is predicted, the maturity of the concrete is predicted by using the steps shown in FIG. 4. The corresponding strength of the concrete can also be determined. In this manner, the method according to the invention, enables one to derive at the estimated time of completion for an element.

In a preferred embodiment according to the invention, for each new data point measured by sensors, a recalculate the entire method is carried out to improve accuracy and improve the data model for estimating the environmental influence.

Figure 6A:
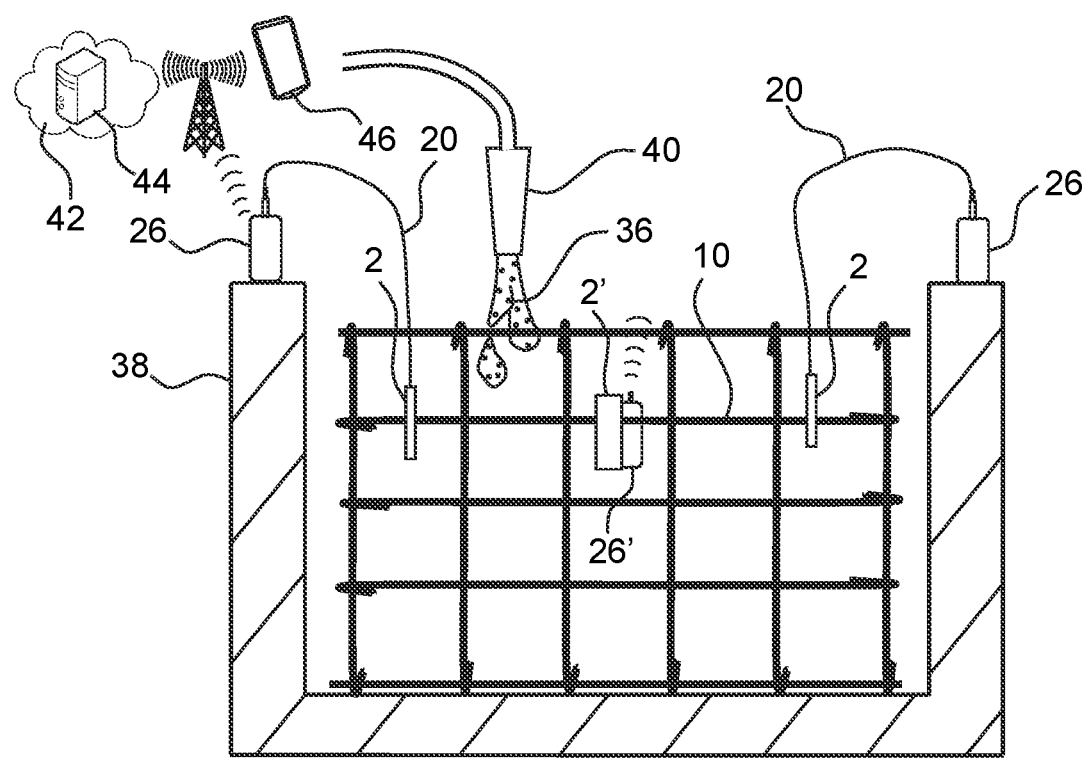
FIG. 6A shows a cross-sectional view of a casting frame and two mounting devices according to the invention each attached to a rod.
Figure 6B:
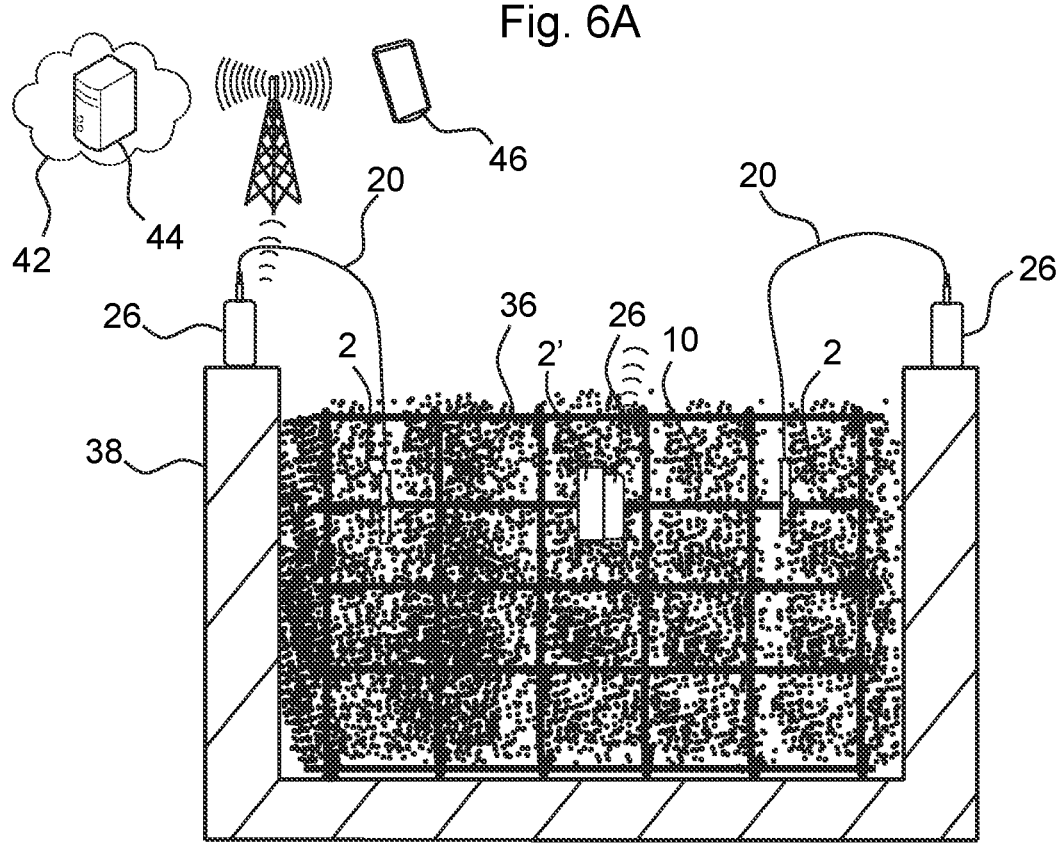
FIG. 6B shows the casting frame shown in FIG. 6A while concrete has been poured into the casting frame.
Figure 7A:
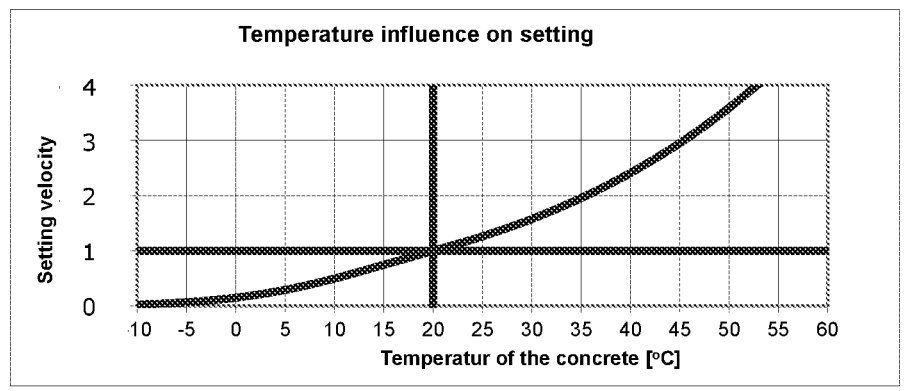
FIG. 7A shows a graph of the relationship between setting of cement, reaction time and temperature.
Figure 7B:
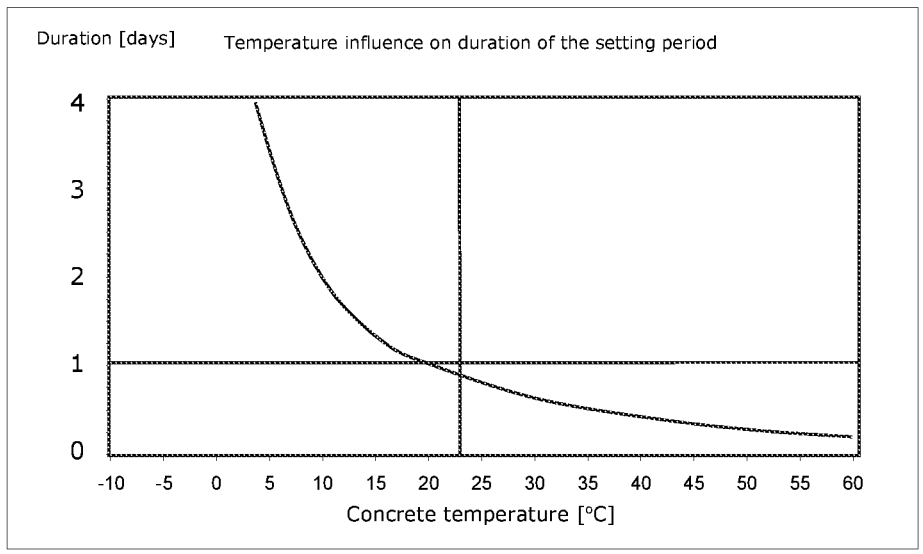
FIG. 7B shows a graph illustrating the relationship between the duration of the setting and the concrete temperature.

FIG. 6A illustrates a cross-sectional view of a casting frame 38 and two mounting devices 2 configured to be used to attach thermocouples to rebar 10. FIG. 6B illustrates the casting frame 38 shown in FIG. 6A while concrete 36 has been poured into the casting frame 38. Concrete 36 is poured into the casting frame 38 by means of a concrete nozzle 40.

The sensors 26 may be configured to communicate wirelessly with an external device such as a server 44 via the Internet 42. The sensors 26 may be configured to communicate directly wirelessly with an external device such as a smartphone 46. The smartphone 46 may communicate wirelessly with the Internet 42 and/or an Internet-based server 44.

In one embodiment according to the invention, the sensor 26' may be integrated in the mounting device 2 or detachably attached to the mounting device 2. Hereby, the server 26' may be attached to a rebar 10 by means of a mounting device 2' according to the invention. In such a solution, wireless communication may be provided between the sensor 26' and an external device such as a server 44 via the Internet 42. The sensors 26' may also be configured to communicate directly and wirelessly with an external device such a smartphone 46.

The rebar 10 is part of a rebar cage (steel mesh). Each mounting device 2 is attached to a cable 20 that is plugged into a sensor 26. The sensors 26 may be configured to perform real-time temperature and maturity monitoring of the concrete 36. The temperature may be detected by means of a cable 20 comprising a thermocouple having two dissimilar conductors forming electrical junctions at differing temperatures which are capable of producing a temperature-dependent voltage.

LIST OF REFERENCE NUMERALS 2, 2' Mounting device
4 Support unit (table with integrated heating unit)
6 Heat from the support unit
8 Heat from the concrete to the surrounding
9 Heat from the surroundings to the concrete
10 Elongated body
12 Electrical connection (socket)
14 Electric plug
16 Humidity sensor
18 Circulating air
20 Cable
22 Airflow sensor
24 Heating unit
26, 26' Sensor
28 Foil
30 Missing curing time
32 Time
34 Temperature
36 Concrete
38 Frame
40 Concrete nozzle
42 Internet
44 Server
46 External device 50 System
52 Strength
54, 56 Curve
X Longitudinal axis
$T_c$ Curing time
E Prior art estimated curing time
$CA_1$, $CA_2$, $CA_3$, $CA_4$ Capacity available
$L_1$, $L_2$, $L_3$, $L_4$, $L_5$, $L_6$ Production line
$\theta_n$, $\theta_{n+1}$, $\theta_1$, $\theta_2$, $\theta_3$, $\theta_4$ Concrete temperature
$\Delta Q_{acc,n}$ Change of accumulated energy in the concrete
$\Delta Q_{trans,n}$ Change of transmitted energy from the concrete
C Content of cement
$\rho_c$ Density of concrete
$C_c$ Specific heat of the concrete
$f_{c,n}$, $f_{c,n+1}$ Output from box wall transducer
$m_c$ Weight of the concrete sample
$a_f$ Calibration factor
Q Heat development
$\Delta t_n$, $\Delta t_1$, $\Delta t_2$, $\Delta t_3$ Time interval $(t_{n+1}-t_n)$
$B_1$, $B_2$, $B_3$, $B_4$, $B_5$ Measurement point
$A_1$, $A_2$, $A_3$, $A_4$ Theoretical point (100% insulation)
$A_5$, $A_6$, $A_7$ Theoretical point (100% insulation)
$Z_1$, $Z_2$, $Z_3$, $Z_4$, $Z_5$, $Z_6$ Projected point
X Environmental influence
I Calculation of maturity
II Projection of internal energy
III Applying environmental influencing factors
IV Estimating concrete temperature

The invention claimed is:

1. A method for predicting a maturity of a concrete during an early-stage curing process, characterized in that the method comprises the following steps:
    predicting at least one future temperature within the concrete by using information about a relationship between temperature and energy production in the concrete, wherein said prediction is carried out after:
        performing at least one real-time temperature measurement of the concrete;
        transmitting the at least one real-time temperature measurement wirelessly from at least one temperature sensor to an external device, wherein said least one temperature sensor is used for performing the at least one real-time temperature measurement of the concrete; and
        by using the external device determining energy production ($\Delta Q_n$) within the concrete, wherein the step of determining the energy production within the concrete is carried out by applying information about the real-time temperature of the concrete;
    wherein in the step of predicting at least one future temperature within the concrete, the temperature used for the prediction is carried out on the basis of a measured temperature being the real-time temperature measurement, and
    wherein the step of performing at least one real-time temperature measurement of the concrete is carried out on a continuous basis.

2. A method according to claim 1, characterized in that the step of transmitting the at least one temperature measurement comprises transmitting the at least one temperature measurement to the external device comprising a server via the internet.

3. A method according to claim 1, characterized in that environmental parameters are saved to form historical data, wherein at least some of the historical data are used for predicting at least one future temperature within the concrete.

4. A method according to claim 3, characterized in that the environmental parameters include at least one of (a) one or more environmental temperatures, (b) one or more air circulation measurements, and (c) one or more humidity measurements.

5. A system for predicting a maturity of a concrete during an early-stage curing process, characterized in that the system comprises:
    a predicting unit configured to predict at least one future temperature within the concrete;
    at least one temperature sensor configured to perform real time temperature measurements of the concrete; and
    an energy production estimator configured to estimate energy production ($\Delta Q_n$) within the concrete,
    wherein the at least one temperature sensor is arranged and configured to transmit at least one temperature measurement wirelessly to an external device and wherein the predicting unit is configured to apply
        a) the real time temperature measurements of the concrete made by the at least one temperature sensor and
        b) the estimated energy production ($\Delta Q_n$) within the concrete estimated by the energy production estimator
    to predict the at least one future temperature,
    wherein the system is configured to carry out at least one real-time temperature measurement of the concrete on a continuous basis.

6. A system according to claim 5, characterized in that the system comprises:
    one or more environmental parameter determination units configured to determine one or more environmental parameters influencing the temperature of the concrete.

7. A system according to claim 5, characterized in that the system is configured to store one or more environmental parameters to form historical data, wherein at least some of the historical data are used for predicting at least one future temperature within the concrete.

8. A system according to claim 5, characterized in that the at least one temperature sensor is configured to transmit the temperature measurements to the external device comprising a server via the internet.

* * * * *